(12) United States Patent
Tanaka et al.

(10) Patent No.: US 7,402,692 B2
(45) Date of Patent: Jul. 22, 2008

(54) INTERMEDIATES IN PRODUCING PHENOXYACETIC ACID DERIVATIVES AND METHOD OF USING THE SAME

(75) Inventors: Nobuyuki Tanaka, Nagano (JP); Tetsuro Tamai, Nagano (JP); Harunobu Mukaiyama, Nagano (JP); Takehiro Ishikawa, Nagano (JP); Junichi Kobayashi, Nagano (JP); Satoshi Akahane, Nagano (JP); Hiromu Harada, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 11/923,067

(22) Filed: Oct. 24, 2007

(65) Prior Publication Data

US 2008/0045739 A1    Feb. 21, 2008

Related U.S. Application Data

(62) Division of application No. 10/526,660, filed as application No. PCT/JP02/09034 on Sep. 5, 2002, now Pat. No. 7,329,771.

(51) Int. Cl.
C07C 229/00 (2006.01)
C07C 69/76 (2006.01)

(52) U.S. Cl. .......................................... 560/42; 580/60
(58) Field of Classification Search ................ 560/42
See application file for complete search history.

(56) References Cited

U.S. PATENT DOCUMENTS 6,774,267 B2   8/2004   Wilhelm et al.

FOREIGN PATENT DOCUMENTS

EP    1095932  A1    5/2001

WO    WO 00/02846   1/2000

OTHER PUBLICATIONS

Tanaka, N., et al., "Beta 3 Adrenoceptor Agonists for the Treatment of Frequent Urination and Urinary Incontinence" 2001, Bioorganic & Medicinal Chemistry, 9, 3265-3271.*

* cited by examiner

Primary Examiner—Yvonne Eyler
Assistant Examiner—Jennifer Y Cho
(74) Attorney, Agent, or Firm—Sughrue Mion, PLLC

(57) ABSTRACT

The present invention provides novel intermediates represented by general formula (I) etc. for preparing a phenoxyacetic acid derivative represented by general formula (X) or a pharmaceutically acceptable salt thereof, which has β3-adrenoceptor stimulating activity and are useful for treating or preventing obesity, hyperglycemia, diseases caused by intestinal hypermotility, pollakiuria, urinary incontinence, depression or biliary calculus. The present invention also provides a process for preparing said intermediates and a method of using said intermediates

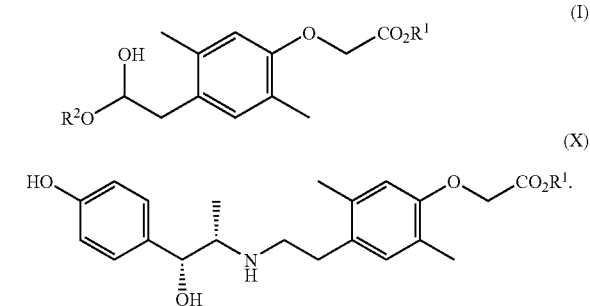

2 Claims, No Drawings

INTERMEDIATES IN PRODUCING PHENOXYACETIC ACID DERIVATIVES AND METHOD OF USING THE SAME

This is a divisional of application Ser. No. 10/526,660 filed Mar. 4, 2005, in the names of Nobuyuki Tanaka et al as a 371 of PCT/JP02/09034 May 9, 2002.

TECHNICAL FIELD

The present invention provides novel intermediates for preparing a phenoxyacetic acid derivative represented by general formula (X):

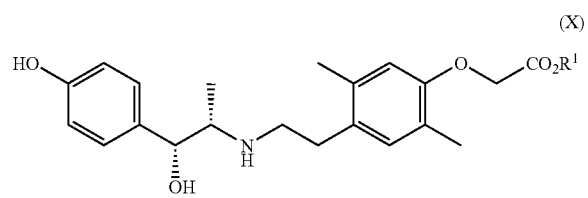

(X)

wherein $R^1$ is a lower alkyl group, or a pharmaceutically acceptable salt thereof, which has β3-adrenoceptor stimulating activity and are useful for treating or preventing obesity, hyperglycemia, diseases caused by intestinal hypermotility, pollakiuria, urinary incontinence, depression or biliary calculus. The present invention also provides a process for preparing said intermediates and a method of using said intermediates.

BACKGROUND ART

WO2000/02846 discloses a process for preparing a phenoxyacetic acid derivative represented by general formula (X), which comprises the step of treating an amine of formula (IX):

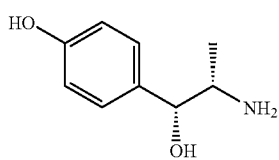

(IX)

with an alkylating agent represented by general formula (XI):

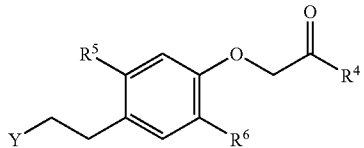

(XI)

wherein $R^4$ is a lower alkoxy group, $R^5$ and $R^6$ are a lower alkyl group, Y is an eliminating group such as a p-toluenesulfonyloxy or methanesulfonyl group, a chlorine, bromine or iodine atom and the like, in the presence or absence of a base. However, WO2000/02846 does not teach or suggest a compound represented by general formula (I) of the present invention.

DISCLOSURE OF THE INVENTION

The present inventors have intensively investigated a novel intermediate which can be transformed into a phenoxyacetic acid derivative of general formula (X) or a pharmaceutically acceptable salt thereof conveniently and in high yield, and found that the phenoxyacetic acid derivative (X) can be prepared from a novel hemiacetal compound represented by general formula (I) in very high yield. Moreover, the present inventors have found a process for preparing the hemiacetal compound (I) from 2,5-xylenol through convenient procedures. Based on these findings, the present invention has been accomplished.

The present invention therefore provides:

(1) a compound represented by general formula (I):

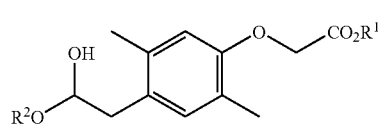

(I)

wherein each of $R^1$ and $R^2$ is independently a lower alkyl group;

(2) the compound according to the above (1), wherein $R^1$ and $R^2$ are an ethyl group;

(3) A process for preparing a compound represented by general formula (I):

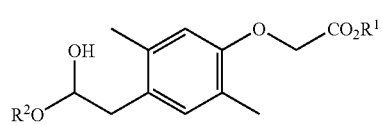

(I)

wherein each of $R^1$ and $R^2$ is independently a lower alkyl group, which comprises the steps of (a) treating a compound represented by formula (II):

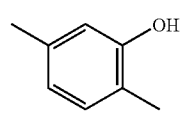

(II)

with a compound represented by general formula (III):

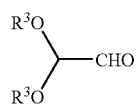

(III)

wherein $R^3$ is a lower alkyl group, to form a compound represented by general formula (IV):

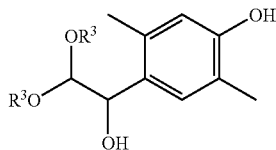

wherein $R^3$ is as defined above;
(b) treating said compound represented by general formula (IV) with a compound represented by general formula (V):

$$ZCH_2CO_2R^1 \qquad (V)$$

wherein Z is a chlorine, bromine or iodine atom, and $R^1$ is as defined above, to form a compound represented by general formula (VI):

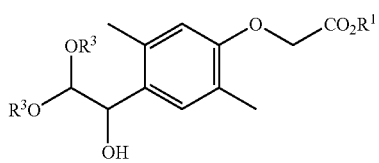

wherein $R^1$ and $R^3$ are as defined above;
(c) reducing said compound represented by general formula (VI) to form a compound represented by general formula (VII):

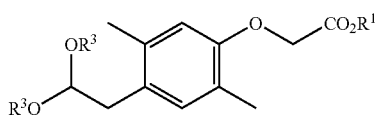

wherein $R^1$ and $R^3$ are as defined above;
(d) hydrolyzing said compound represented by general formula (VII) to form a compound represented by general formula (VIII):

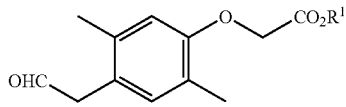

wherein $R^1$ is as defined above; and
(e) treating said compound represented by general formula (VIII) with $R^2$—OH wherein $R^2$ is as defined above;
(4) the process according to the above (3), wherein $R^1$ and $R^2$ are an ethyl group, and $R^3$ is a methyl group;
(5) a compound represented by general formula (IV):

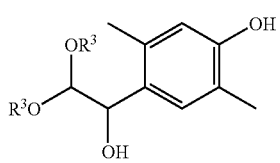

wherein $R^3$ is a lower alkyl group;
(6) the compound according to the above (5), wherein $R^3$ is a methyl group;

(7) a compound represented by general formula (VI):

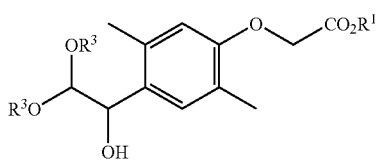

wherein each of $R^1$ and $R^3$ is independently a lower alkyl group;
(8) a compound represented by general formula (VII):

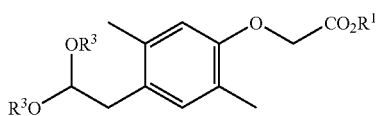

wherein each of $R^1$ and $R^3$ is independently a lower alkyl group;
(9) the compound according to the above (7) or (8), wherein $R^1$ is an ethyl group, and $R^3$ is a methyl group;
(10) a compound represented by general formula (VIII):

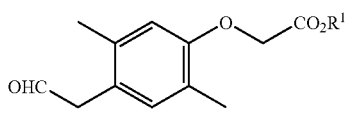

wherein $R^1$ is a lower alkyl group;
(11) the compound according to claim 1, wherein $R^1$ is an ethyl group;
(12) A process for preparing a compound represented by general formula (X):

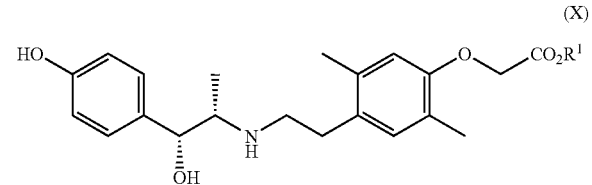

or a pharmaceutically acceptable salt thereof, wherein $R^1$ is a lower alkyl group, which comprises the step of treating a compound represented by general formula (I):

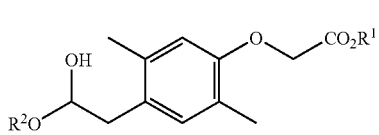

wherein $R^1$ is as defined above, and $R^2$ is a lower alkyl group, with a compound represented by formula (IX):

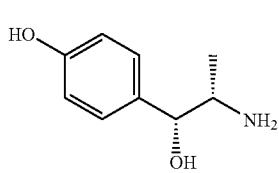

(IX)

in the presence of a reducing agent, and thereafter optionally forming a pharmaceutically acceptable salt of said compound (X)

(13) the process according to the above (12), wherein $R^1$ and $R^2$ are an ethyl group.

In the present invention, the term "lower alkyl group" refers to a straight chained or branched alkyl group having 1 to 6 carbon atoms such as a methyl, ethyl, propyl, isopropyl, butyl, isobutyl, sec-butyl group and the like.

BEST MODE FOR CARRYING OUT THE INVENTION

A compound represented by general formula (I) of the present invention can be prepared through steps (a) to (e) as illustrated in the following scheme.

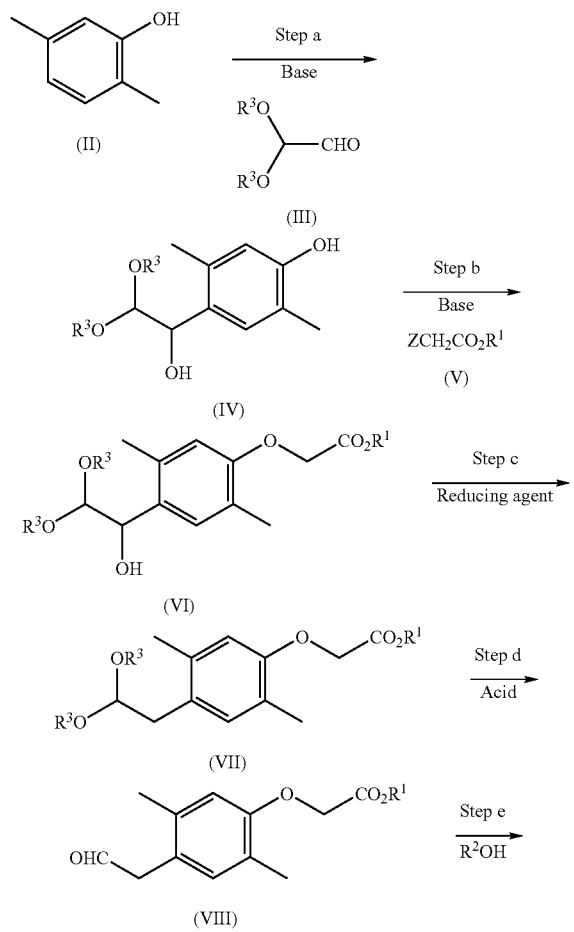

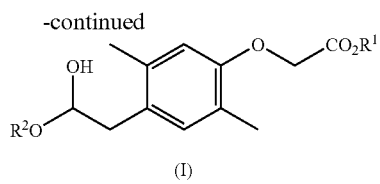

(I)

wherein $R^1$, $R^2$, $R^3$ and Z are as defined above.

(Step a)

A phenol derivative represented by general formula (IV) can be prepared by treating 2,5-xylenol represented by formula (II) with a compound represented by general formula (III) in the presence of an aqueous solution of alkali metal hydroxide such as an aqueous solution of sodium hydroxide. The amount of compound (III) and alkali metal hydroxide is used ordinarily in the range of about 1 to about 3 molar equivalents based on 1 mole of 2,5-xylenol (II). The reaction is ordinarily carried out at a temperature of about 10 to about 70° C. for a period of 1 to 10 hours. After the reaction is finished, the reaction solution is neutralized with a dilute acid such as diluted hydrochloric acid. Thereafter, the precipitating crystals are filtered and dried to afford a phenol derivative of general formula (IV).

(Step b)

The phenol derivative (IV) is treated with a haloacetic acid ester of general formula (V) in the presence of a base in an inert solvent to afford a compound represented by general formula (VI). The inert solvents employed in the reaction include ethers such as tetrahydrofuran or the like, ketones such as acetone, methyl ethyl ketone or the like, acetonitrile, N,N-dimethylformamide, N,N-dimethylacetamide or the like. The solvents may be used singly or as a mixture of two or more solvents. The base employed in the reaction includes sodium carbonate, potassium carbonate, cesium carbonate or the like. Haloacetic acid ester (V) includes $ClCH_2CO_2R^1$, $BrCH_2CO_2R^1$ or $ICH_2CO_2R^1$. The amount of haloacetic acid (V) and a base is used ordinarily in the range of about 1 to about 5 molar equivalents based on 1 mole of phenol derivative (IV). Haloacetic acid ester (V) and a base are ordinarily used in an equimolar ratio, but either of them may be used in excess. The reaction is carried out ordinarily at a temperature of about 0 to about 100° C. for a period of 1 to 24 hours. After the reaction is finished, extraction of the reaction mixture and further concentration according to conventional procedures afford a compound of general formula (VI).

(Step c)

Reduction of the compound (VI) using a reducing agent in an inert solvent affords an acetal derivative represented by general formula (VII). The inert solvents employed in the reaction include ethers such as tetrahydrofuran, 1,2-dimethoxyethane, dioxane or the like, organic carboxylic acid esters such as ethyl acetate or the like, acetonitrile or the like. The solvents may be used singly or as a mixture of two or more solvents. Reducing agents employed in the reaction include sodium iodide/trialkylchlorosilane such as chlorotrimethylsilane, chlorotriethylsilane, t-butyl-dimethylchlorosilane or the like, which are ordinarily used in an amount of about 2 to about 6 molar equivalents based on 1 mole of compound (VI). The reaction is carried out ordinarily at a temperature of about −30 to about 30° C. for a period of 10 minutes to 12 hours. After the reaction is finished, extraction of the reaction mixture and further concentration according to conventional procedures afford an acetal derivative of general formula (VII).

(Step d)

Hydrolysis of the acetal derivative (VII) using an acid in a suitable solvent affords an aldehyde derivative represented by general formula (VIII). The solvent employed in the hydrolysis reaction includes ethers such as tetrahydrofuran, 1,2-dimethoxyethane, dioxane or the like, ketones such as acetone or the like, acetonitrile or the like. The solvents may be used singly or as a mixture of two or more solvents. The solvents may also be used in combination with water. The acid employed in the reaction includes 5-20% perchloric acid, 1-10% hydrochloric acid, 1-10% sulfuric acid, p-toluenesulfonic acid, trifluoroacetic acid or the like, which is used ordinarily in an amount of about 0.1 to about 2.5 molar equivalents based on 1 mole of the acetal derivative (VII). The hydrolysis reaction is carried out ordinarily at a temperature of about 0 to about 50° C. for a period of 0.5 to 24 hours. After the reaction is finished, extraction of the reaction mixture and further concentration according to conventional procedures afford an aldehyde derivative (VIII).

(Step e)

A hemiacetal derivative represented by general formula (I) of the present invention can be prepared by treating the aldehyde (VIII) with $R^2OH$, optionally in the presence of an acid such as acetic acid or the like. The addition reaction of $R^2OH$ to the aldehyde derivative (VIII) proceeds rapidly, and the subsequent crystallization from a suitable solvent affords a hemiacetal derivative of general formula (I). The amount of $R^2OH$ is used ordinarily in the range of about 1 to about 10 molar equivalents based on 1 mole of the aldehyde (VIII). In the case of using an acid, the amount of the acid is used ordinarily in the range of about 0.01 to about 0.1 molar equivalents based on 1 mole of the aldehyde (VIII). The solvents for crystallization include a mixed solvent of $R^2OH$ in combination with n-hexane, n-heptane, cyclohexane or the like. The hemiacetal derivative (I) exhibits good crystalline property, and can be stored under a particular condition, for example below 10° C., for a long period. Accordingly, the hemiacetal are suitable for a commercial production.

A process for preparing a phenoxyacetic acid derivative of general formula (X), which is useful as a medicament, using a hemiacetal derivative of general formula (I) is detailed in the following scheme.

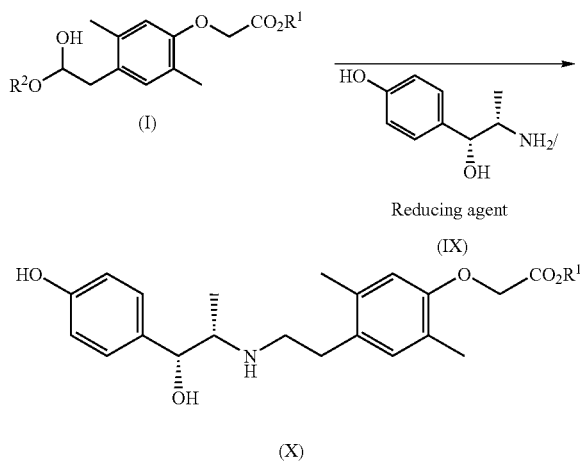

wherein $R^1$ and $R^2$ are as defined above.

A phenoxyacetic acid derivative represented by general formula (X) can be prepared by treating a hemiacetal derivative of general formula (I) with an amine of formula (IX) in the presence of a reducing agent in an inert solvent. The inert solvents employed in the reaction include ethers such as tetrahydrofuran, 1,2-dimethoxyethane, dioxane or the like, halogenated hydrocarbons such as methylene chloride, 1,2-dichloroethane or the like, organic carboxylic acids such as acetic acid or the like, hydrocarbons such as toluene or the like, alcohols such as methanol, ethanol or the like, acetonitrile or the like. The solvents may be used singly or as a mixture of two or more solvents. The reducing agents employed in the reaction include alkali metal hydroboranes such as $NaBH_4$, $NaBH_3CN$, $NaBH(OAc)_3$, $NaBH(OMe)_3$ or the like, boranes such as $BH_3 \cdot$pyridine, $BH_3 \cdot$N,N-diethylaniline or the like. If necessary, these reducing agents may be used optionally in the presence of an acid such as acetic acid, p-toluenesulfonic acid, methanesulfonic acid, sulfuric acid, hydrochloric acid, or a base such as triethylamine or the like. Alternatively, the reaction can be carried out under a hydrogen atmosphere in the presence of a metal catalyst such as 5-10% palladium on carbon, Raney-Ni, platinum oxide, palladium black, 10% platinum on carbon (sulfided) or the like. In the case of using alkali metal hydroboranes or boranes as a reducing agent, such reducing agent is used ordinarily in the range of about 0.5 to about 5 molar equivalents based on 1 mole of the hemiacetal derivative (I). The reaction is carried out ordinarily at a temperature of about 0 to about 60° C. for a period of 1 to 48 hours. After the reaction is finished, if required, insoluble materials are filtered off, and extraction of the reaction mixture and further concentration according to conventional procedures afford a phenoxyacetic acid derivative of general formula (X). Alternatively, the reaction can be carried out by treating an amine (IX) with an aldehyde of general formula (VIII) in place of a hemiacetal derivative (I).

The phenoxyacetic acid derivative (x) can be optionally converted to a pharmaceutically acceptable acid addition salt thereof according to conventional methods. Examples of such salts include acid addition salts formed with mineral acids such as hydrochloric acid, hydrobromic acid, hydroiodic acid, sulfuric acid, phosphoric acid and the like; acid addition salts formed with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic aid, glutamic acid, aspartic acid and the like.

An amine represented by formula (IX) can be prepared by optically separating a commercially available enantiomeric mixture of the amine according to conventional methods. Alternatively, the amine (IX) can be prepared according to procedures as described in "J. Med. Chem., 1997, 20(7), p. 978-981".

A compound represented by general formula (I) of the present invention, its intermediates (IV), (VI), (VII) and (VIII) as well as a phenoxyacetic acid derivative of general formula (X) can be optionally isolated or purified through standard isolation or purification techniques such as solvent extraction, recrystallization, chromatography and the like.

EXAMPLE

The following examples illustrate the invention in further detail. It is to be understood, however, that they are not to be construed as limiting the scope of the invention in any way.

Example 1

4-(1-Hydroxy-2,2-dimethoxyethyl)-2,5-dimethylphenol

A suspension of an aqueous solution of 5.2% sodium hydroxide (630 g), 2,5-xylenol (100 g), an aqueous solution of 60% glyoxal dimethyacetal (213 g) and water (200 g) was heated at 55° C. for 5 hours with stirring. The reaction mixture was cooled in an ice bath, and to the mixture were added acetonitrile (90 g) and 7.4% hydrochloric acid (380 g) successively. The precipitating crystals were filtered to give 4-(1-hydroxy-2,2-dimethoxyethyl)-2,5-dimethylphenol (150 g).

$^1$H-NMR (DMSO-d$_6$) δ ppm: 2.06 (3H, s), 2.15 (3H, s), 3.08 (3H, s), 3.35 (3H, s), 4.23 (1H, d, J=6.7 Hz), 4.55 (1H, dd, J=6.7, 4.4 Hz), 4.96 (1H, d, J=4.4 Hz), 6.49 (1H, s), 7.03 (1H, s), 8.96 (1H, s)

Example 2

Ethyl 2-[4-(1-hydroxy-2,2-dimethoxyethyl)-2,5-dimethyl-phenoxy]acetate

To N,N-dimethylformamide (81 g) were added 4-(1-hydroxy-2,2-dimethoxyethyl)-2,5-dimethylphenol (20.0 g), potassium carbonate (15.8 g) and ethyl chloroacetate (12.4 g) at room temperature with stirring. The mixture was stirred at room temperature for an hour, and then stirred at 71° C. for 2 hours. The reaction mixture was diluted with ethyl acetate, washed with water and brine, and dried over anhydrous sodium sulfate. The organic layer was concentrated under reduced pressure, and a mixture of ethyl acetate and hexane was added to the residue. The precipitated crystals were collected by filtration to give ethyl 2-[4-(1-hydroxy-2,2-dimethoxyethyl)-2,5-dimethyl-phenoxy]acetate (21.3 g).

$^1$H-NMR (CDCl$_3$) δ ppm: 1.28 (3H, t, J=7.1 Hz), 2.26 (3H, s), 2.32 (3H, s), 2.54 (1H, d, J=2.3 Hz), 3.22 (3H, s), 3.50 (3H, s), 4.27 (2H, q, J=7.1 Hz), 4.32 (1H, d, J=6.6 Hz), 4.61 (2H, s), 4.80 (1H, dd, J=6.6, 2.3 Hz), 6.48 (1H, s), 7.25 (1H, s)

Example 3

Ethyl 2-[4-(2,2-dimethoxyethyl)-2,5-dimethylphenoxy]acetate

To a stirred suspension of sodium iodide (72 g) and chlorotrimethylsilane (52 g) in acetonitrile (180 g) was added dropwise a solution of ethyl 2-[4-(1-hydroxy-2,2-dimethoxyethyl)-2,5-dimethylphenoxy]acetate (50 g) in acetonitrile (80 g) in an ice-salt bath. The mixture was stirred for 30 minutes, and then toluene (400 g) and pyridine (25 g) were added. The reaction mixture was washed with an aqueous solution of sodium thiosulfate, an aqueous solution of citric acid, an aqueous solution of sodium bicarbonate and brine successively. The organic layer was dried over anhydrous sodium sulfate, and concentrated under reduced pressure to give ethyl 2-[4-(2,2-dimethoxyethyl)-2,5-dimethylphenoxy]acetate (43 g).

$^1$H-NMR (CDCl$_3$) δ ppm: 1.30 (3H, t, J=7.1 Hz), 2.24 (3H, s), 2.27 (3H, s), 2.82 (2H, d, J=5.6 Hz), 3.33 (6H, s), 4.27 (2H, q, J=7.1 Hz), 4.47 (1H, t, J=5.6 Hz), 4.60 (2H, s), 6.50 (1H, s), 6.97 (1H, s)

Example 4

Ethyl 2-[4-(2-formylmethyl)-2,5-dimethylphenoxy]acetate

Ethyl 2-[4-(2,2-dimethoxyethyl)-2,5-dimethylphenoxy]acetate (23.7 g) was dissolved in acetonitrile (110 g) with stirring, and 10% perchloric acid (120 g) was added, and then the mixture was stirred for an hour at room temperature. The reaction mixture was partitioned between toluene (190 g) and water (120 g). The organic layer was washed with water, an aqueous solution of sodium bicarbonate and brine successively, and dried over anhydrous sodium sulfate, followed by concentration under reduced pressure. After the residue was dissolved in ethanol (96 g), the solvent was removed under reduced pressure. The residue was dissolved with ethanol (96 g) again, and removal of the solvent under reduced pressure gave ethyl 2-[4-(2-formylmethyl)-2,5-dimethylphenoxy]acetate (20.8 g).

$^1$H-NMR (CDCl$_3$) δ ppm: 1.30 (3H, t, J=7.1 Hz), 2.20 (3H, s), 2.25 (3H, s), 3.59 (2H, d, J=2.4 Hz), 4.27 (2H, q, J=7.1 Hz), 4.62 (2H, s), 6.56 (1H, s), 6.94 (1H, s), 9.66 (1H, t, J=2.4 Hz)

Example 5

Ethyl 2-[4-(2-ethoxy-2-hydroxyethyl)-2,5-dimethylphenoxy]acetate

Ethyl 2-[4-(2,2-dimethoxyethyl)-2,5-dimethylphenoxy]acetate (43 g) was dissolved in acetonitrile (190 g) while stirring. To the resulting solution was added 10% perchloric acid (216 g), and the mixture was stirred for an hour at room temperature. The reaction mixture was partitioned between toluene (340 g) and water (200 g). The organic layer was washed with water, an aqueous solution of sodium bicarbonate and brine successively, and dried over anhydrous sodium sulfate, followed by concentration under reduced pressure. The residue was dissolved in ethanol (180 g), and the solvent was removed under reduced pressure. The residue was dissolved with hexane (86 g) and ethanol (37 g). After seed crystals were added, the solution was stirred at 0-10° C. for 2 hours. Hexane (220 g) was added, and the resulting suspension was stirred at 0-10° C. for 2 hours. The precipitated crystals were filtered to give ethyl 2-[4-(2-ethoxy-2-hydroxyethyl)-2,5-dimethylphenoxy]acetate (21 g).

$^1$H-NMR (DMSO-d$_6$) δppm: 1.06 (3H, t, J=7.0 Hz), 1.21 (3H, t, J=7.1 Hz), 2.11 (3H, s), 2.19 (3H, s), 2.50-2.80 (2H, m), 3.20-3.40 (1H, m), 3.60-3.70 (1H, m), 4.16 (2H, q, J=7.1 Hz), 4.50-4.70 (1H, m), 4.73 (2H, s), 5.98 (1H, d, J=7.6 Hz), 6.59 (1H, s), 6.93 (1H, s)

Example 6

Ethyl (−)-2-[4-[2-[[(1S,2R)-2-hydroxy-2-(4-hydroxyphenyl)-1-methyethyl]amino]ethyl]-2,5-dimethylphenoxy]acetate A suspension of ethyl 2-[4-(2-ethoxy-2-hydroxyethyl)-2,5-dimethylphenoxy]acetate (5.4 g), 10% palladium carbon (50% wet, 1.4 g), (1R,2S)-2-amino-1-(4-hydroxyphenyl)propan-1-ol (3.0 g) and tetrahydrofuran (30 g) was stirred under a hydrogen atmosphere at 40° C. for 3 hours. After the catalyst was removed by filtration, the filtrate was concentrated under reduced pressure. The residue was dissolved in toluene, and washed with water, an aqueous solution of sodium bicarbonate and brine successively. The organic layer was dried over anhydrous sodium sulfate, and the solvent was removed under reduced pressure to give ethyl (−)-2-[4-[2-[[(1S,2R)-2-hydroxy-2-(4-hydroxyphenyl)-1-methyethyl]amino]ethyl]-2,5-dimethylphenoxy]acetate (7.3 g).

$^1$H-NMR (CDCl$_3$) δppm: 0.98 (3H, d, J=6.4 Hz), 1.34 (3H, t, J=7.1 Hz), 2.18 (3H, s), 2.22 (3H, s), 2.60-3.00 (5H, m), 4.31 (2H, q, J=7.1 Hz), 4.49 (1H, d, J=5.6 Hz), 4.62 (2H, s), 6.41 (1H, s), 6.69 (2H, d, J=8.5 Hz), 6.78 (1H, s), 7.05 (2H, d, J=8.5 Hz)

Example 7

Ethyl (−)-2-[4-[2-[[(1S,2R)-2-hydroxy-2-(4-hydroxyphenyl)-1-methyethyl]amino]ethyl]-2,5-dimethylphenoxy]acetate hydrochloride A suspension of ethyl 2-[4-(2-ethoxy-2-hydroxyethyl)-2,5-dimethylphenoxy]acetate (68.7 g), 10% palladium carbon (50% wet, 17 g), (1R,2S)-2-amino-1-(4-hydroxyphenyl)propan-1-ol (38.0 g) and tetrahydrofuran (380 g) was stirred under a hydrogen atmosphere at 40° C. for 5 hours. After the catalyst was removed by filtration, the filtrate was concentrated under reduced pressure. The residue was dissolved in toluene, and washed with water, an aqueous solution of sodium bicarbonate and brine successively. The organic layer was dried over anhydrous sodium sulfate, and the solvent was removed under reduced pressure. The residue was dissolved in toluene (200 g) and ethanol (21 g), and 20 weight % hydrogen chloride in ethanol (37.3 g) was added dropwise.

The precipitated crystals were filtered to give ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride (70.2 g).

$^1$H-NMR (DMSO-$d_6$) δppm: 0.96 (3H, d, J=6.6 Hz), 1.21 (3H, t, J=7.1 Hz), 2.15 (3H, s), 2.25 (3H, s), 2.8-3.2 (4H, m), 4.16 (2H, q, J=7.1 Hz), 4.76 (2H, s), 4.9-5.1 (1H, m), 5.8-6.0 (1H, m), 6.68 (1H, s), 6.76 (2H, d, J=8.5 Hz), 6.96 (1H, s), 7.17 (2H, d, J=8.5 Hz), 8.5-9.0 (2H, br), 9.41 (1H, s)

INDUSTRIAL APPLICABILITY

Via a hemiacetal derivative represented by general formula (I) of the present invention, a phenoxyacetic acid derivative of general formula (X) or pharmaceutically acceptable salt thereof can be prepared from a commercially available 2,5-xylenol in high purities and through convenient procedures. Therefore, said hemiacetal derivative (I) is useful as a intermediate for preparing a medicament for treating or preventing obesity, hyperglycemia, diseases caused by intestinal hypermotility, pollakiuria, urinary incontinence, depression or biliary calculus.

The invention claimed is:

1. A process for preparing a compound represented by general formula (X):

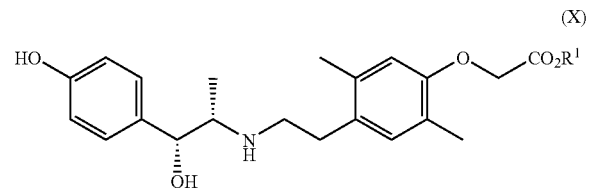

(X)

or a pharmaceutically acceptable salt thereof, wherein $R^1$ is a lower alkyl group, which comprises the step of treating a compound represented by general formula (I):

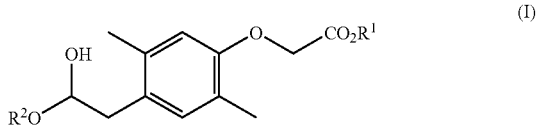

(I)

wherein $R^1$ is as defined above, and $R^2$ is a lower alkyl group, with a compound represented by formula (IX):

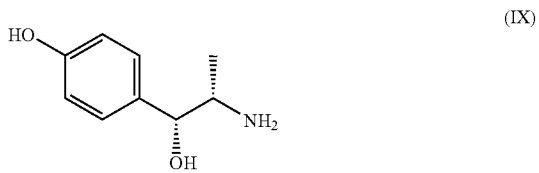

(IX)

in the presence of a reducing agent, and thereafter optionally forming a pharmaceutically acceptable salt of said compound (X).

2. The process according to claim 1, wherein $R^1$ and $R^2$ are an ethyl group.

* * * * *